US008816000B2

(12) United States Patent
Rong et al.

(10) Patent No.: US 8,816,000 B2
(45) Date of Patent: Aug. 26, 2014

(54) MULTIFUNCTIONAL STELLATE PREPOLYMER MIXTURES, PRODUCTION AND USE AND COATINGS MADE THEREOF

(75) Inventors: Haitao Rong, Darmstadt (DE); Peter Greiwe, Heidelberg (DE); Jürgen Groll, Aachen (DE); Christine Mohr, Bebra (DE); Marina Glesius, Ober-Ramstadt (DE); Martin Möller, Aachen (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 452 days.

(21) Appl. No.: 12/709,559

(22) Filed: Feb. 22, 2010

(65) Prior Publication Data

US 2010/0209613 A1    Aug. 19, 2010

Related U.S. Application Data

(63) Continuation of application No. PCT/EP2008/060194, filed on Aug. 4, 2008.

(30) Foreign Application Priority Data

Aug. 22, 2007   (DE) .......................... 10 2007 039 648

(51) Int. Cl.
   *C08G 83/00* (2006.01)
(52) U.S. Cl.
   CPC .............. *C08G 83/00* (2013.01); *C08G 83/002* (2013.01)
   USPC ................ 524/731; 427/387; 528/10; 528/41
(58) Field of Classification Search
   CPC .............................. C08G 83/00; C08G 83/002
   USPC ........................... 427/387; 528/10, 41; 524/73
   See application file for complete search history.

(56) References Cited

U.S. PATENT DOCUMENTS

| 5,171,264 | A  | * | 12/1992 | Merrill ............................ 623/3.1 |
| 6,423,661 | B1 |   | 7/2002  | McGraw et al. |
| 7,998,919 | B2 | * | 8/2011  | Rong et al. ..................... 510/466 |
| 2002/0042471 | A1 |   | 4/2002 | Lomoelder et al. |
| 2003/0027921 | A1 |   | 2/2003 | Speier et al. |
| 2003/0153712 | A1 |   | 8/2003 | Ludewig et al. |
| 2004/0030031 | A1 | * | 2/2004 | Martin et al. ................. 524/502 |
| 2004/0096507 | A1 | * | 5/2004 | Kwang et al. ................. 424/486 |
| 2005/0031793 | A1 | * | 2/2005 | Moeller et al. ................ 427/384 |
| 2009/0029043 | A1 | * | 1/2009 | Rong et al. ..................... 427/180 |
| 2010/0209612 | A1 | * | 8/2010 | Rong et al. ..................... 427/331 |
| 2010/0209613 | A1 | * | 8/2010 | Rong et al. ..................... 427/387 |

FOREIGN PATENT DOCUMENTS

| DE | 102004031938 A1 | 1/2005 |
| DE | 10332849 A1 | 2/2005 |
| EP | 0335308 A2 | 10/1989 |
| EP | 0935627 A1 | 5/1999 |
| EP | 0931800 A1 | 7/1999 |
| WO | 9112886 A1 | 9/1991 |
| WO | 9325247 A1 | 12/1993 |
| WO | 9952574 A1 | 10/1999 |
| WO | 9955765 A1 | 11/1999 |

OTHER PUBLICATIONS

Fabbri, E. et al. Perfluorcpolyether-Silica Hybrids: Preparation and Surface Characterization. Journal of Sol-Gel Science and Technology. 34 (2005) 155-163.

* cited by examiner

*Primary Examiner* — Michael Pepitone
*Assistant Examiner* — Michael A Salvitti
(74) *Attorney, Agent, or Firm* — Ingrassia Fisher & Lorenz, P.C.

(57) ABSTRACT

The invention relates to coatings having a contact angle hysteresis with water measured by the sessile drop method of at most 20°. The coatings can be produced from a mixture of at least two different stellate prepolymers and/or stellate prepolymer/nanoparticle complexes which may cross-link to each other and to the surface of the substrate coated, wherein the stellate prepolymers and/or stellate prepolymer/nanoparticle complex have at least three hydrophilic polymer branches before cross-linking which are themselves soluble in water with on all or a part of the free ends thereof, silyl end groups $R^1$ of general formula (I): $R^1=-CR^a{}_2-Si(OR^b)_r(R^c)_{3-r}$, where $R^a$=H or straight or branched chain 1-6C alkyl, $OR^b$=a hydrolysable group, $R^c$=linear or branched chain 1-6C alkyl and r=a number from 1 to 3 and the optionally non silyl end group carrying ends have reactive end groups which a reactive with each other, with the substrate to be coated optional entities included in the coating and/or with the silyl end groups with the proviso the mixture (a) has at least one stellate prepolymer with 3-5 hydrophilic polymer branches and (b) at least one stellate prepolymer and/or a stellate prepolymer/nanoparticle complex with a least 6 hydrophilic polymer branches. The invention further relates to a method for production for said coatings and stellate prepolymers as used in the coatings. The invention furthermore relates to the use of the stellate prepolymers as additives in various materials for temporary or permanent anti-soiling treatment of surfaces.

13 Claims, No Drawings

MULTIFUNCTIONAL STELLATE PREPOLYMER MIXTURES, PRODUCTION AND USE AND COATINGS MADE THEREOF

CROSS REFERENCE TO RELATED APPLICATIONS

The present application is a continuation of International Patent Application No. PCT/EP2008/060194 filed 4 Aug. 2008, which claims priority to German Patent Application No. 10 2007 039 648.3 filed 22 Aug. 2007, both of which are incorporated herein by reference.

The present invention relates to coatings based on mixtures of different self-crosslinking stellate prepolymers and/or stellate prepolymer-nanoparticle complexes having hydrophilic polymer arms with hydrolyzable silyl and/or siloxyl end groups on their free ends, as well as the production of coatings based thereon. In addition, the invention relates to mixtures of stellate prepolymers suitable for such coatings, their production and use in a variety of fields of application.

In various fields of application such as medicine, bioanalysis, cosmetics, technical equipment, textile finishing, textiles, household goods, hygiene and the antifouling field, there is a demand for finishing surfaces that repel dirt and microbial impurities (both proteins and cells) (soil repellency) and/or facilitate their release/washability (soil release). Since dirt, proteins, various polymers or cells typically adhere well to hydrophobic materials, there is a special demand for surfaces having a hydrophilic finish.

Hydrophilic coatings to date include hydrogel coatings based on polyethylene oxides and/or polyethylene glycols. Various methods noted below are proposed for producing such coatings.

WO 9952574 A1 describes a biomolecule-repellent coating produced by immobilizing a terminal, linear, trichlorosilane-modified polyethylene glycol on vitreous surfaces.

WO 9112886 A1 and WO 9325247 A1 describe a hydrogel coating produced from stellate polyethylene oxides with the help of electron bombardment.

EP 335308 A2 describes the use of prepolymers of polyethylene oxide diols and triols whose terminal OH groups have been reacted with polyisocyanates for producing coatings having a low nonspecific protein adsorption.

WO 03063926A1 discloses an ultra thin hydrogel coating produced from stellate isocyanate-terminated prepolymers having polyether polymer arms. Such hydrogel coatings effectively suppress nonspecific protein absorption on surfaces finished with them.

In addition, DE 102004031938 A1 and DE 10332849 A1 describe the use of such hydrogel coating in hygiene and bioanalytical fields.

Although hydrogel coatings described in the art cause a reduction in adsorption of cells and protein to different extents, complex production processes for these coatings prevent large-scale use in many cases.

This includes, for example, use of reactive coating materials synthesizable only by complex methods and are difficult to handle, use of expensive irradiation installations, or the obligatory use of adhesion promoters, necessitating complex coating operations.

Production of hydrophilic hydrogel coatings without the use of adhesion promoters wherein the coatings are anchored on substrate surfaces with a stable covalent bond and are obtained by a simple method, and wherein the coating operations are greatly simplified and a large-scale spectrum of application is made possible is not known from the art.

Therefore, there is a demand for improving the production process for such hydrogel coatings so that use of adhesion promoters may be omitted while coatings having long-term stability are still obtained.

In addition to reducing the adhesion tendency of microorganisms, it is favorable for cleaning reasons to provide surfaces with hydrophilic properties because such surfaces are easily wetted with typical washing liquids on an aqueous basis, thus facilitating washing processes (soil release). However, these surfaces would have to be finished at the same time so that the water can run off as completely as possible after wetting, leaving no film of water on the surface.

Hydrophilic surfaces known from the art are more or less completely wetted with water or with water-based cleaning solutions. However, the water either forms a stable film on the surface or only runs off to a minor extent. This has the disadvantage in that, on drying out, a water film remains as residual soiling on the surface. Thus, mineral deposits such as lime scale deposits, among others, remain that tend to promote renewed soiling—even by proteins and microorganisms. Therefore, there is a need for hydrophilic surfaces that facilitate wetting and soil release while at the same time are easily "dewetted" from a water film.

A dewetting coating based on perfluoropolyethers and silica (from tetraethoxyorthosilane, TEOS) is known from Fabbri et al., *J. Sol-Gel Science and Technologies*, 34 (2005), pp. 155-163; however, this coating has a large water contact angle (i.e., a relatively high hydrophobicity). Fabbri et al. also describes fluorine-free and pure TEOS coatings (i.e., $SiO_{2-x/2}(OH)_x$) having a hysteresis of 3.6° with contact angles of approximately 56-58°.

However, coatings of the present invention are also able to provide a broad spectrum of properties, including adjusting wettability, water swellability, protein and cell repellency, as well as mechanical and thermal stability in a targeted manner in order to finish the coatings, thereby enabling them to meet various requirements at the same time.

The present invention provides these properties as well as overcomes the disadvantages of the prior art regarding high hydrophobicities and low dewetting properties by providing coatings having a contact angle hysteresis of water as measured by the sessile drop method and the tilting plate method, of at most 20°. This is accomplished by using a contact angle measuring device equipped with a tiltable measurement table, a video measurement system and automatic evaluation software. The coatings are manufactured from a mixture comprising at least two different stellate prepolymers and/or stellate prepolymer-nanoparticle complexes that are mutually crosslinkable and crosslinkable with the surface of the substrate to be coated. The stellate prepolymers and/or stellate prepolymer-nanoparticle complexes have at least three hydrophilic polymer arms prior to being crosslinked, wherein the arms are each water-soluble and have silyl end groups $R^1$ of the following general formula I on some or all of their free ends—

$$R^1 \text{ is } -CR^a{}_2-Si(OR^b)_r(R^c)_{3-r} \qquad (I)$$

wherein $R^a$ is hydrogen or a linear or branched alkyl group with one to six carbon atoms; $OR^b$ is a hydrolyzable group; $R^c$ is a linear or branched alkyl group with one to six carbon atoms; and r is a number from 1 to 3, wherein the silyl end groups $R^1$ are not bound at the end of the polymer arm via a polyisocyanate (which also includes diisocyanates), and have reactive and/or functional groups on the ends that do not have silyl end groups and are optionally present, these reactive and/or functional groups being self-reactive, with the substrate to be coated, entities optionally introduced into the coating and/or with the silyl end groups, with the proviso that the mixture contains: (a) at least one stellate prepolymer having three to five hydrophilic polymer arms and (b) at least one stellate prepolymer and/or stellate prepolymer-nanoparticle complex having at least six hydrophilic polymer arms.

By incorporating the two different stellate components (a) and (b) defined above, hybrid-type coatings have been obtained which allow a more targeted adjustment of different properties in comparison with coatings made of only one single stellate prepolymer, and which surprisingly allow an improved and therefore also more stable surface coverage.

Stellate prepolymers according to the present invention have polymer arms bound to a central unit, wherein the polymer arms are bound substantially in a stellate and/or radial pattern to the central unit so that one end of the polymer arm is bound to the central unit while the other end is not bound to it.

Stellate prepolymer-nanoparticle complexes according to the present invention further include those having polymer arms bound to nanoparticles, wherein the polymer arms are bound to the nanoparticle in a substantially stellate and/or radial pattern so that one end of the polymer is bound to the surface of the nanoparticle while another end is not bound to its surface.

Preferred embodiments of coatings according to the invention are described below.

Suitable stellate prepolymers and/or stellate prepolymer-nanoparticle complexes used in the coating include those in which the stellate prepolymer and/or the stellate prepolymer-nanoparticle complex have multiple polymer chains bound to a central unit, wherein the central unit is preferably a low-molecular organochemical central unit for the stellate prepolymer, and is preferably an inorganic oxidic nanoparticle for the stellate prepolymer-nanoparticle complex.

Such stellate prepolymers and/or stellate prepolymer-nanoparticle complexes used in coatings according to the invention have the following general formula II—

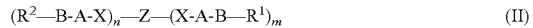

$$(R^2\text{—}B\text{-}A\text{-}X)_n\text{—}Z\text{—}(X\text{-}A\text{-}B\text{—}R^1)_m \qquad (II)$$

wherein Z is the central unit, wherein, for stellate prepolymers, this defines the number of arms of the stellate prepolymer; A is a hydrophilic, separately water-soluble polymer arm; B and X are independently a chemical bond or a divalent, low-molecular organic radical having preferably 1 to 50 carbon atoms, in which the silyl end groups $R^1$ are not bound at the end of the polymer arm by a polyisocyanate and/or diisocyanate; $R^2$ is a group which is self-crosslinkable and/or crosslinkable with $R^1$ or the substrate; and m and n are each integers, such that in the case of the stellate prepolymers, m≥1 and n≥0, and m+n have a value of 3 to 100; in the case when at least one $R^2$ radical stands for an isocyanate radical, m+n have a value of 4 to 100, corresponding to the number of arms of Z, and the m (X-A-B—$R^1$) groups as well as the n (X-A-B—$R^2$) groups may have different meanings, independent of one another; in the case of the prepolymer-nanoparticle complexes, m≥1 and n≥0, and m+n have a value of 3 to a maximum of 500,000.

With respect to the stellate prepolymers, Z preferably is a glycerol radical or a polyvalent sugar (e.g., sorbitol or sucrose). In principle, however, all initiator molecules known in the art and used to produce stellate prepolymers may be used to form the Z radical.

With respect to the stellate prepolymer-nanoparticle complexes, Z preferably is a nanoparticle of silica, zinc oxide, aluminum oxide, zirconium oxide, calcium carbonate, titanium dioxide, carbon, magnesium oxide or iron oxide. Nanoparticles of group Z are available commercially or are synthesized in situ or ex situ, preferably by sol-gel processes, precipitation from aqueous or nonaqueous solution, gas-phase synthesis (flame pyrolysis, chemical vapor deposition, etc.), or by mechanical machining (e.g. milling, ultrasound). These especially preferably have a size of 0.5 to 200 nm, most especially preferably from 0.5 to 20 nm.

With respect to the stellate prepolymer-nanoparticle complexes, polymer arms A are preferably bound to the nanoparticle surface of the Z radical via hydrolyzable silyl end groups. However, the bonding may also be accomplished via other groups reacted with the surface (e.g., carboxyl groups, cationic groups (e.g. trialkylammonium groups), phosphonate groups, etc.). Linear polyoxyalkylenediols, in which two OH groups are reacted with silanes that are reactive with OH groups (e.g., isocyanatosilanes) are especially suitable for introduction of the polymer arms on the nanoparticle. Other compounds suitable for introduction of the polymer arms on the nanoparticle include polyether polyol (e.g., VORANOL®, TERRALOX®, SYNALOX® and DOWFAX® from Dow Chemical Corporation, SORBETH® from Glyco Chemicals, Inc., GLUCAM® from Amerchol Corp., or Lupranol® and Pluronic® from BASF).

Wettability of coatings according to the invention with water is a sensitive measure of their hydrophilicity or hydrophobicity. The contact angle of a drop of water on a planar substrate with air as the ambient medium results from the surface energies of the coating and of water as well as the interfacial energy between water and the coating according to Young's equation. In the case of maximal hydrophilicity, the contact angle approaches 0°. In the case of maximal hydrophobicity, the contact angle approaches 180°. In the present invention, the hydrophilicity and/or hydrophobicity of the coatings may also be influenced through choice of different stellate prepolymers. Thus, stellate prepolymers (a) having three to five hydrophilic polymer arms—with the same polymer arm structure and same polymer arm length—are usually more hydrophobic than stellate prepolymers (b) having at least six hydrophilic polymer arms. This difference between the prepolymers can be utilized in coating different surfaces by varying the ratio of the components (a) and (b) of the mixture, depending on the surface coated.

In practice, the sessile drop method and the tilting plate method are often used to determine static contact angle and contact angle hysteresis of a drop of liquid on a surface. For example, when a water drop is deposited on a real horizontal surface, the water forms a symmetrical drop, where the measured contact angle is known as the static contact angle (sessile drop method). While the surface is slowly inclined, the water drop undergoes an asymmetrical deformation accordingly. Beyond a certain tilt angle, the drop begins to move. Two contact angles are measured, a larger angle (advancing) and a smaller angle (receding). In the ideal case, the difference between the two should be zero. In actuality, there is a difference, which is also known as contact angle hysteresis and is attributed to surface roughness, inhomogeneities and impurities. The lower the hysteresis value, the better the "dewetting" of the coating from the adhering water.

Coatings according to the invention preferably have a static water contact angle of no more than 90°, or better, no more than 70°, especially preferably no more than 50° and most especially preferably no more than 45°. In many cases water contact angles of 40° and less are achieved.

Coatings according to the invention whose contact angle hysteresis in water is no more than 20°, especially preferably no more than 18° and most especially preferably no more than 15°, measured according to the sessile drop method and the tilting plate method, are preferred. Contact angle hystereses of no more than 10° or even 2°, 3° or 4° and less are achieved in additional preferred cases.

In a special embodiment, coatings are obtained from mixtures of stellate prepolymers according to general formula (II), wherein the radical $OR^b$ is an alkoxy radical, especially preferably a methoxy or ethoxy radical, and r=1, 2 or 3, especially preferably 2 or 3. Examples of $R^1$ radicals include dimethylethoxysilyl-$CR^a{}_2$, dimethylmethoxysilyl-$CR^a{}_2$, diisopropylethoxy-silyl-$CR^a{}_2$, methyldimethoxysilyl-$CR^a{}_2$, methyldiethoxysilyl-$CR^a{}_2$, trimethoxysilyl-$CR^a{}_2$, triethoxysilyl-$Cle_2$ or tri-t-butoxysilyl-$CR^a{}_2$ radicals.

B in the stellate prepolymer of general formula (II) is a chemical bond or a divalent, low-molecular organic radical preferably having 1 to 50 C atoms, in particular 2 to 20 C atoms. Examples of divalent, low-molecular organic radicals include aliphatic, heteroaliphatic, araliphatic, heteroaraliphatic, cycloaliphatic, cycloheteroaliphatic and aromatic and heteroaromatic radicals. Short-chain aliphatic and heteroaliphatic radicals are especially preferred. Examples of suitable radicals include aminopropyl, N-(2-aminoethyl)(3-aminopropyl), 3-methacryloxypropyl, metharyloxymethyl, 3-acryloxypropyl, 3-isocyanatopropyl, isocyanatomethyl, butyraldehyde, 3-glycidoxypropyl, propylsuccinic anhydride, chloromethyl, 3-chloropropyl, hydroxymethyl.

In particular, coatings obtained from mixtures of stellate prepolymers and/or stellate prepolymer-nanoparticle complexes of general formula (II) are preferred, wherein two vicinal B radicals or all B radicals in the B—$R^1$ group cannot create more than one hydrogen bridge, preferably no hydrogen bridges to one another. Such a coating having little crosslinking by hydrogen bridges allows for greater flexibility in the orientation of the polymer arms A, which in turn results in a more uniform distribution of the prepolymers and/or prepolymer-nanoparticle complexes, yielding a uniform closed coating. In addition, presence of a particularly large number of crosslinkings and/or especially strong crosslinkings through hydrogen bridge bonds causes the materials to be too viscous for them to be usable in typical application formulations.

Therefore, especially preferred coatings include those in which the radical B of the stellate prepolymers of general formula (II) in the group B—$R^1$ contains at most one urethane group, one ester, or one urea group.

In another preferred embodiment, the present invention relates to coatings made of crosslinked stellate prepolymers of general formula (II), wherein the $R^2$ radical is preferably chosen from isocyanate radicals, (meth)acrylate radicals, oxirane radicals, alcoholic OH groups, primary and secondary amino groups, thiol groups and silane groups. If silane groups are used as the $R^2$ groups, they may also have general formula (I), but they must differ from $R^1$ in at least one of the groups $R^a$, $R^b$ and $R^c$ and/or the numerical value of r. Groups suitable as additional $R^2$ groups include, for example, carboxylic acid groups, carboxylic acid ester groups, lactone, lactam and carboxylic anhydride groups, carboxylic and sulfonic acid halide groups, active ester groups, radically polymerized C=C double bonds, e.g., in addition to the aforementioned (meth)acryl groups, also vinyl ether and vinyl ester groups, also activated C=C double bonds, activated C≡C triple bonds and N=N double bonds, which react without alkyl group in the sense of an en-reaction or with conjugated diolefin groups in the sense of a Diels-Alder reaction. Examples of groups capable of reacting with allyl groups in the sense of an en-reaction or with dienes in the sense of a Diels-Alder reaction include maleic acid and fumaric acid groups, maleic acid ester and fumaric acid ester groups, cinnamic acid ester groups, propiolic acid (ester) groups, maleic acid amide and fumaric acid amide groups, maleimide groups, azodicarboxylic acid ester groups and 1,3,4-triazoline-2,5-dione groups. In coatings, $R^2$ is especially preferably an isocyanate, oxirane or OH group.

One advantage of hydrogel coating according to the invention versus known hydrogel coatings is that its properties are definable in a targeted manner through an appropriate choice of $R^1$ and $R^2$ radicals, as well as their ratio to one another and the ratio of components (a) and (b) of the mixture. Thus, for example, wettability, water swellability and protein and cell repellency may be influenced through targeted adjustment of the $R^1/R^2$ ratio.

Coatings according to the invention contain mixtures of stellate prepolymers whose polymers arms, separately, are water-soluble. The preferred stellate prepolymers of general formula (II) preferably have polymer arms A, which are selected from the group consisting of poly-$C_2$-$C_4$-alkylene oxides, polyoxazolidones, polyvinyl alcohols, homopolymers and copolymers containing at least 50 wt % N-vinylpyrrolidone polymerized into them, homopolymers and copolymers containing at least 30 wt % acrylamide and/or methacrylamide polymerized into them, homopolymers and copolymers containing at least 30 wt % acrylic acid and/or methacrylic acid polymerized into them. Especially preferred are polymer arms A consisting of polyethylene oxide or ethylene oxide/propylene oxide copolymers. If the most especially preferred ethylene oxide/propylene oxide copolymers are used, then a propylene oxide content of no more than 50 wt %, preferably no more than 40 wt % and especially preferably no more than 25 wt %, based on the sum of the weight of propylene oxide units (iso-$C_3H_6O$) and ethylene oxide units ($C_2H_4O$), is recommended.

The indices m and n of the stellate prepolymers used in the coatings and/or stellate prepolymer-nanoparticle complexes each represent integers, where m≥1 and n≥0, and m+n preferably have a value of 3 to 100 in the case of the stellate prepolymers and preferably have a value of 3 up to a maximum value of 500,000 in the case of prepolymer-nanoparticle complexes.

In the case of the stellate prepolymers, indices m and n each represent integers, where m≥1 and n≥0, and m+n preferably have a value of 3 to 100 or 3 to 50, in particular 3 to 10, and match the number of arms of Z. The central unit therefore usually has 3 to 100, preferably 3 to 50, in particular 3 to 10 structural atoms serving as attachment points for the arms. Mixture component (a)—the stellate prepolymer having three to five hydrophilic polymer arms—used in the coating according to the invention or the mixture according to the invention preferably has three or four, especially preferably three hydrophilic polymer arms. The additional mixture component (b)—the stellate prepolymer and/or the stellate prepolymer-nanoparticle complex having at least six hydrophilic polymer arms—preferably has six to ten, especially preferably six to eight polymer arms.

In the case of stellate prepolymer-nanoparticle complexes, the indices m and n each represent integers, where m≥1 and n≥0, and m+n preferably have a value of 3 to 500,000.

In an especially preferred embodiment, n is 0, and the stellate prepolymer corresponds to a completely $R^1$-modified prepolymer preferably having 5 to 50, and especially preferably 4 to 10 polymer arms. When n>0, the ratio n/m varies between 99/1 and 1/99, preferably 49/1 and 1/49, and in particular 9/1 and 1/9.

Stellate prepolymers in coatings and mixtures according to the invention can be obtained, for example, by reacting compounds of the general formula Z—(X-A-Y)$_{m+n}$ (wherein Z, X, A, m and n are as defined above) with silanes reactive with the Y group. Y is preferably a hydroxyl or amino group. In such a case, suitable reactive silanes include isocyanatosilanes such as (3-isocyanatopropyl)trialkoxysilane (e.g., (3-isocyanatopropyl)trimethoxysilane, (3-isocyanatopropyl) triethoxysilane, (isocyanatomethyl)methyldimethoxysilane and (isocyanatomethyl)-trimethoxy-silane), aldehyde silanes, such as triethoxysilylundecanal and triethoxysilylbutyraldehyde, epoxysilanes (e.g., (3-glycidoxypropyl)-trimethoxysilane), anhydride silanes (e.g., 3-(triethoxysilyl) propylsuccinic anhydride), and halo-silanes (e.g., chloromethyl-trimethoxysilane, 3-chloropropylmethyl-dimethoxysilane). If Y is OH, then compounds of general formula $Z—(X-A-Y)_{m+n}$ are preferably polyether polyols. Compounds of general formula $Z—(X-A-Y)_{m+n}$ preferably have a number-average molecular weight in the range of 200 to 50,000, especially preferably 1000 to 30,000 and most especially preferably 5000 to 20,000 g/mol. The number-average molecular weight is determined as described in the Examples.

The stellate prepolymer preferably contains at least 0.05 wt % silicon, especially preferably at least 0.1 wt %, and most especially preferably at least 0.15 wt %.

In a special embodiment, coatings according to the invention further contain foreign materials of an organic, inorganic or natural origin, referred to below simply as "entities". An entity is preferably chosen from biologically active substances, pigments, dyes, fillers, silicic acid units, nanoparticles, organosilanes, biological cells, receptors or molecules or cells having receptors and physically incorporated into the coating and/or covalently bonded thereto.

Examples of such entities include biologically active materials such as active ingredients, biocides, oligonucleotides, peptides, proteins, signal substances, growth factors, cells, carbohydrates and lipids, inorganic components such as apatite and hydroxylapatite, quaternary ammonium salt compounds, compounds of bisguanidines, quaternary pyridinium salt compounds, compounds of phosphonium salts, thiazoylbenzimidazoles, sulfonyl compounds, salicylic compounds or organometallic and inorganometallic compounds. Antibacterial substances such as peptides, metal colloids and quaternary ammonium and pyridinium salt compounds are preferred.

Another important group of entities include organically functionalized silanes (organosilanes) of the type $(R')_{1+x}Si(OR'')_{3-x}$ (x=0, 1 or 2). Characteristic here is the simultaneous presence of silicic acid ester groups (OR''), which hydrolyze in an aqueous solution to form condensable silanol groups (Si—OH) as well as hydrolysis-stable Si—R' bonds on the same silicon atom, the latter hydrolysis-stable bond usually consisting of a covalent Si—C single bond. These functionalized silanes are often low-molecular compounds, but oligomeric or polymeric compounds also fall under the heading of "organically functionalized silanes"; therefore, the Si—OR'' groups that are hydrolyzable to silanol groups as well as nonhydrolyzable Si—R' groups are present in the same molecule. With the [usually organic] R' groups in the functionalized silanes, it is possible to incorporate the entire bandwidth of additional chemical functionalities into the coatings described here. For example, cationic adhesion groups (e.g., $NR'''_3^+$ groups), anionic adhesion groups (e.g., $SO_3^-$), redox-active groups (e.g., quinone/hydroquinone radicals), dye groups (e.g., azo dye molecules, brighteners based on stilbene), groups with a biological/pharmacological efficacy (e.g., also saccharide and/or polysaccharide molecular units, peptides and/or protein units and other organic structural motifs), groups for covalent bonding to substrates (e.g. epichlorohydrin radicals, cyanuric chloride, cystine/cysteine units and the like), groups with a bactericidal efficacy (e.g., $NR'''_3^+$ groups with very long R''' alkyl radicals), catalytically active groups (e.g., transition metal complexes with organic ligands) may be incorporated into the layer in this way. Additional groups introduced via the R' radical include, for example, epoxy, aldehyde, acrylate and methacrylate groups, anhydride, carboxylate or hydroxyl groups. Functionalities described here are by no means to be understood as a complete list in the sense of a selection of examples. The organosilanes therefore serve not only as a crosslinking aid but also as a functionality-imparting agent. This directly yields a hydrogel coating according to the invention having the desired functionalities.

These entities also include nanoparticulate metal oxides or semimetal oxides. Suitable examples include silicon, zinc, titanium, aluminum and zirconium. Silicon oxide particles having a diameter of approximately 1 to 500 nm are especially preferred. Such $SiO_2$ particles, including their surface-modified and/or functionalized derivatives, may contribute toward an improvement in the mechanical properties of the layers.

Another group of useful entities are inorganic pigments. Coatings according to the invention having reactive silyl groups easily bind to them via stable covalent bonds. If a hydrogel according to the invention (i.e., a coating according to the invention mixed with pigments) is applied to a surface to which the hydrogel can bind, bound pigmented surface coatings result. If organic pigments are incorporated into the hydrogel and/or if adhesion of the hydrogel to organic surfaces is required, then organosilanes having the appropriate adhesion groups can be incorporated into the coating according to the invention (e.g., cationic groups as described above). In this way, agents and methods by which pigments can be anchored well on hair, for example, become possible. For example, if mica or effect pigments (pearlized pigment) are bound to hair, then special optical effects are made possible ("glitter hair"). By using colored organic or inorganic pigments (e.g., lapis lazuli, pyrolopyrroles), especially intense and/or stable hair colors are obtained.

The entities are preferably incorporated by co-adsorption from solutions containing mixtures of the stellate prepolymers and/or stellate prepolymer-nanoparticle complexes and the foreign component. Furthermore, the stellate prepolymers and/or prepolymer-nanoparticles complexes can be chemically reacted with the biologically active materials or brought to reaction on the surface as a mixture with unmodified stellate prepolymers and/or prepolymer-nanoparticle complexes. It is also possible to apply the foreign substances in a targeted manner to a finished hydrogel coating according to the invention by physisorption or chemisorption.

Substrates coated with coatings according to the invention are not subject to any restrictions. The substrates can be regularly or irregularly shaped, smooth or porous surfaces.

Suitable surface materials include, for example, vitreous surfaces such as glass, quartz, silicon, silicon dioxide or ceramic or semiconductor materials, metal oxides, metals and metal alloys such as aluminum, titanium, zirconium, copper, tin and steel. Compounds of materials such as glass fiber-reinforced (GFR) plastics or carbon fiber-reinforced plastics (CFRP), polymers such as polyvinyl chloride, polyethylene, polymethylpentenes, polypropylene, polyolefins in general, elastomeric plastics such as polydimethylsiloxane, polyesters, fluoropolymers, polyamides, polyurethanes, polymethacrylates as well as copolymers, blends and composites of the aforementioned materials are suitable as substrates. In addition, cellulose, and natural fibers such as cotton fibers, wool and hair may also be used as substrates. Mineral surfaces such as paints or joint sealing material may also be used as the substrate. For polymer substrates, in some cases the surfaces may need to be pretreated. Especially preferred substrate materials are vitreous and/or inorganic surfaces in general, because binding by relatively hydrolysis-stable bonds (e.g., Si—O—Si or Si—O—Al) occurs directly with these surfaces, and thus no surface pretreatment is necessary. If direct formation of covalent (hydrolysis-stable) bonds between hydrogel and substrate does not succeed by the method described above, for example, in the presence of organic substrate surfaces (Si—O—C bonds are hydrolysislabile), then bonding may be accomplished by adding organofunctional silanes having adhesive groups. Suitable adhesive groups include, for example, cationic trimethylammonium groups or amino groups. Due to the simultaneous presence of reactive siloxy groups, these functional groups are incorporated into the hydrogel and also become an integral, covalently-bonded component of the coating.

In particular, in the field of glass, ceramic, plastic and metal substrates, this is useful in the finishing of showers, windows, aquariums, glasses, utensils, wash basins, toilets, working surface or kitchen appliances such as refrigerators or stoves having an easily cleanable temporary or permanent finish, allowing water to run off completely as well as repell proteins and bacteria.

Another subject of the present invention is a method for producing the coatings on a substrate, wherein a solution of the mixture of (a) and (b) (as defined above) is applied to the substrate to be coated, and an at least partial self-crosslinking reaction of the silyl end groups and the reactive groups (optionally present) of the non-silyl-end-group-carrying ends that do not have silyl end groups and/or crosslinking with the substrate takes place before, simultaneously or subsequently.

Preferred embodiments of the method according to the invention are described below.

The method is preferably performed using mixtures of the stellate prepolymers and/or stellate prepolymer-nanoparticle complexes of general formula (II).

In a preferred embodiment of the method according to the invention, a foreign material (e.g., biologically active substances, pigments, dyes, fillers, silicic acid units, nanoparticles, organosilanes, biological cells, receptors or molecules or cells having receptors or precursors of the aforementioned entities) is brought into contact with the stellate prepolymers before, during and/or after applying a solution of the mixture of (a) and (b) to the substrate to be coated. Entities thereby introduced may be physically incorporated into the network of the crosslinked stellate prepolymers and/or stellate prepolymer-nanoparticle complexes or ionically bound to the surface of the coating by van der Waals bonds or hydrogen bridge bonds or chemically bound by covalent bonds, preferably by reactive end groups of the stellate prepolymers.

For example, if silicic acid units are introduced as entities in the coating, this can be accomplished by mixing a solution of the mixture of (a) and (b) with a hydrolyzable silicic acid precursor such as a tetraalkoxysilane (e.g., tetraethoxyorthosilane, TEOS), preferably in the presence of a catalyst such as an acid or a base. The weight ratio of $SiO_2$ of the silicic acid units introduced, based on polyethylene/polypropylene oxide proportion in the coating, is preferably 0.01 to 100, especially preferably 0.5 to 50, and most especially preferably 1 to 10. Binding of the silicic acid units to the stellate prepolymer can be accomplished by van der Waals bonds, ionically, or by hydrogen bridges. However, the bonding is preferably covalent via a C—Si—O—Si constellation (Raman or IR detection) to reactive end groups of the stellate prepolymers and/or stellate prepolymer-nanoparticle complexes used in the coatings according to the invention.

The water contact angle of a coating according to the invention, measured by the sessile drop method on a smooth planar surface, is preferably 0.0001° to 90°, especially preferably 0.001° to 70° and most especially preferably up to 50° or no more than 45°. The water contact angle hysteresis, measured by the tilting plate method, is preferably no more than 18°, especially preferably no more than 15°.

Self-binding of these silicic acid units can take place via hydrogen bridges in the coating or by ionic interaction. However, covalent Si—O—Si bridges are preferred (detectable by IR). The effect of TEOS within the layer may be understood as a crosslinking effect, in which layers without crosslinking agent (TEOS) are usually more hydrophilic (i.e., are characterized by a smaller contact angle). In general, incorporation of additional crosslinking agents such as TEOS and/or functional alkoxysilanes is another way of adjusting the properties of the coatings individually.

Ultra thin hydrogel coatings can be applied to the substrate (e.g., by deposition of the mixtures of (a) and (b) according to essentially known methods on the surface to be coated) from a solution of the three polymers, which may already be partially precrosslinked therein, and simultaneous or subsequent self-crosslinking of the reactive groups and crosslinking to the substrate surface.

In general, all known coating methods may be used. Examples include dip coating, spin coating, polishing and spray methods. To achieve the desired properties of the surface layer, the coating procedures are selected so that the coating thickness does not exceed a value of preferably 500 μm, especially preferably 200 μM and most especially 100 μm. Depending on the intended applications, a coating must simultaneously fulfill many different requirements such as mechanical properties, water wetting and dewetting behavior, protein and bacteria repellency and the like. For many cases, in particular in the household area, a thin or ultrathin layer having a layer thickness of 0.1 to 100 nm, in particular 1 to 50 nm, is often sufficient to achieve the desired effects, whereas thicker layers such as 50-500 μm are preferred for applications in which, for example, there is a high mechanical stress on the surface, and for many applications, those in which nanoparticles are provided in the coating, even greater layer thicknesses up to 1000 μm, for example, may be desired. In contrast with other hydrophilic hydrogel coatings known from the prior art, the hydrophilicity remains largely unaffected by the layer thickness with hydrogel coatings according to the invention. In other words, the properties of repelling soil, protein and cells are preserved, regardless of layer thickness.

Another subject of the present invention is mixtures of the stellate prepolymers of general formula (II), where m and n are independently ≥1, and $R^2$ is not $R^1$ or OH, wherein the mixture (a) contains at least one stellate prepolymer having three to five hydrophilic polymer arms and (b) at least one stellate prepolymer having at least six hydrophilic polymer arms, preferably six to ten polymer arms and especially preferably six to eight polymer arms Mixtures according to the invention of component (a) and (b) and/or mixtures of component (a) and (b) used in coatings according to the invention preferably contains, based on sum of the proportions by weight of components (a) and (b), at least 50 wt % of component (b), especially preferably at least 60 wt % of component (b), most especially preferably 65 to 95 wt % of component (b), such as 70 to 90 wt % of component (b).

To prepare a solution of the stellate prepolymer for the method according to the invention for producing a coating on a substrate, all solvents having little or no reactivity with the reactive end groups of the stellate prepolymer are suitable. Examples include water, alcohols, water/alcohol mixtures, aprotic solvents or mixtures of same.

Examples of suitable aprotic solvents include ethers and cyclic ethers such as tetrahydrofuran (THF), dioxane, diethyl ether, tert-butylmethyl ether, aromatic hydrocarbons such as silane and toluene, acetonitrile, propionitrile and mixtures of these solvents. If stellate prepolymers having OH, SH, carboxyl, (meth)acryl and oxirane groups or similar groups are used as terminal groups, then protic solvent such as water or alcohols (e.g., methanol, ethanol, n-propanol, 2-propanol, n-butanol and tert-butanol as well as mixtures thereof) with aprotic solvents are also suitable. If stellate prepolymers having isocyanate groups are used, then in addition to the aforementioned aprotic solvents, water and mixtures of water with aprotic solvents are also suitable. The solvent is preferably water and/or a mixture of water with aprotic solvents.

Suitable quantities of mixtures of (a) and (b) in the application mixtures used for the coating hi the method according to the invention depend on the layer thicknesses which are most suitable for the particular application. Quantities of approximately 0.005 to 50 wt %, preferably 0.1 to 10 wt % are often sufficient. Depending on affinity of the substrate and the type of application, application mixtures having a higher or even a lower content of the mixtures according to the invention or the mixtures used in the coatings according to the invention may also be used. The application mixtures may also be in the form of pastes or creams, for example.

Stellate prepolymers according to the invention of general formula (II), which are used in the coatings according to the invention and the method for production of a coating according to the invention, are synthesized by functionalizing suitable stellate prepolymer precursors by analogy with known functionalization methods from the prior art.

Prepolymer precursors of the prepolymers according to the invention are also stellate prepolymers already having the stellate structure described above (i.e., at least three polymer arms, each being separately water-soluble, and each having a suitable functional group $R^3$, which may be converted to B—$R^1$ and/or B—$R^2$ in the aforementioned reactive groups) at the ends of the polymer arms. The prepolymer precursors of prepolymers according to the invention can be represented by general formula (III) as Z—$(X-A-R^3)_{m+n}$, where Z, X, A, m and n have the same meanings as the corresponding radicals and indices of the stellate prepolymers used in the mixtures according to the invention, and $R^3$ is a functional group which can be converted to the reactive groups B—$R^1$ and/or B—$R^2$.

The possible functional groups $R^3$ include, for example, OH groups, thiol groups, primary or secondary amine groups and halogen atoms, such as chlorine, bromine or iodine, bound to aliphatic or aromatic carbon atoms. An especially preferred precursor relates to the primary and secondary OH groups, the so-called stellate polyether polyols. These prepolymer precursors are synthesized by polymerization of suitable monomers using small polyfunctional molecules, e.g. sorbitol as the initiator, and may be further modified, if applicable, to create an $R^3$ group according to the invention at their ends. Because of the statistical nature of the polymerization reaction, the statements made above about the polymer arms of the prepolymers according to the invention, in particular with regard to the arm length and number of arms (m+n), are understood to be a statistical mean.

As a rule, all functional silane derivatives having a functional group reactive with the terminal groups of the prepolymer precursor may be used as starting materials for converting the end groups $R^3$ of the stellate prepolymer precursor into the groups B—$R^1$. Examples include aminosilanes such as (3-aminopropyl)triethoxysilane and N-(2-aminoethyl)(3-aminopropyl)-trimethoxysilane, (meth)acrylate silanes such as (3-methacryloxypropyl)trimethoxysilane, (methacryloxymethyl)triethoxysilane, (methacryloxymethyl)methyldimethoxysilane and (3-acryloxypropyl)trimethoxysilane, isocyanatosilanes such as (3-isocyanatopropyl)trimethoxysilane, (3-isocyanatopropyl)triethoxysilane, (isocyanatomethyl)methyldimethoxysilane and (isocyanatomethyl)trimethoxysilane, aldehyde silanes, such as triethoxysilylundecanal and triethoxysilylbutyraldehyde, epoxysilanes, such as (3-glycidoxypropyl)trimethoxysilane, anhydride silanes, such as 3-(triethoxysilyl)propylsuccinic anhydride, halosilanes such as chloromethyltrimethoxysilane, 3-chloropropylmethyldimethoxysilane, hydroxysilanes such as hydroxymethyltriethoxysilanes, and tetraethyl silicate (TEOS), which are available commercially (e.g., from Wacker Chemie GmbH (Burghausen), Gelest, Inc. (Morrisville, USA) or ABCR GmbH & Co. KG (Karlsruhe)) or can be synthesized by known methods. Isocyanatosilanes and/or anhydride silanes having hydroxy-terminated ($R^3$=OH) stellate polymers of general formula (III) are especially preferably reacted. In a complete reaction of all hydroxy termini with isocyanatosilanes, stellate prepolymers used in the mixtures according to the invention are obtained containing exclusively $R^1$ radicals. In such a case, group B contains a urethane group and the atomic group which is positioned between the isocyanato group and the silyl in the starting isocyanatosilane. In a complete reaction of all hydroxy termini with anhydride silanes (e.g., 3-(triethoxysilyl)propyl-succinic anhydride), stellate prepolymers according to the invention containing exclusively $R^1$ radicals are obtained. In such a case, the B group contains an ester group and the atomic group which stands between the anhydride group and the silyl group in the starting anhydride silane.

As a rule, all diisocyanates (both aromatic and aliphatic) can be starting materials for conversion of the end groups $R^3$ of the stellate prepolymer precursor into the groups B—$R^2$, preferably an isocyanate group. Diisocyanates whose isocyanate groups differ in reactivity are preferred; in particular aliphatic and cycloaliphatic diisocyanates such as isophorone diisocyanate (IPDI). In the reaction of hydroxy-terminated stellate prepolymers with diisocyanates, urethane groups are also formed in the B radical. The "B" radical may, however, have different meanings in each of the m+n polymer arms within the stellate prepolymers according to the invention.

If stellate prepolymers according to the invention of general formula (II) having both B—$R^1$ and B—$R^2$ groups are synthesized, then the procedure is preferably to first introduce B—$R^1$ groups as described above, but not all $R^3$ groups in the stellate prepolymer of general formula (III) are reacted. This yields stellate prepolymers having both $R^1$ and $R^2$ groups; this includes the special case in which $R^2$ is the same as $R^3$. For example, in a partial reaction of all hydroxyl termini with isocyanatosilanes, stellate prepolymers according to the invention having both $R^1$ groups, i.e. silyl groups as well as OH groups ($R^2$=$R^3$) are obtained. In another step, some or all of the remaining $R^3$ groups may be modified to $R^2$ radicals and B—$R^2$ radicals, as described above. For example, when $R^2$ is a (meth)acrylate group, methacrylic anhydride is obtained by esterification of the remaining OH groups. In most cases, this is also possible in a reverse reaction sequence, i.e. the $R^3$ group of the stellate prepolymer is first converted to $R^2$ and then to a functional alkoxysilane to introduce the $R^1$ group.

Another subject of the present invention is derivatives of mixtures according to the invention obtained by reaction of the $R^1$ and $R^2$ groups with the aforementioned entities.

In addition to the mixtures according to the invention of stellate prepolymers, other stellate prepolymers may also be used to form the coatings according to the invention as long as they fulfill the conditions according to the invention as defined in claim 1.

In the simplest embodiments, certainly only the minimal requirements of the coatings according to the invention are met. For example, mixtures of stellate prepolymers in which the molecules having silyl groups are linked via diisocyanates are less suitable for forming uniformly dense coatings than are mixtures of stellate prepolymers of general formula (II), in which B contains at most one urethane bond or urea bond. Dense layers in particular allow protection of the substrates from a much broader spectrum of soiling.

Stellate prepolymers known from the art may be used only under the aforementioned prerequisites in coatings according to the invention and in the coating method according to the invention.

EP 0931800 A1 describes a silylated polyurethane produced by first reacting a polyol with a substoichiometric amount of diisocyanate and subsequent reaction of the resulting isocyanate hydroxypolyol with isocyanatosilanes.

US 2003 0153712 A1 describes a polyurethane prepolymer having terminal alkoxysilane groups and hydroxyl groups. For synthesis, a polyether diol was first reacted with a substoichiometric amount of diisocyanate, the resulting isocyanate hydroxy compound was then reacted further with an aminosilane to introduce the silyl groups.

EP 0935627 A1 describes a polyether-based stellate prepolymer having two differently reactive functional groups $R^1$ and $R^2$ on its free ends. $R^1$ here stands for an isocyanate group, while $R^2$ represents a group which is not reactive with $R^1$ under normal conditions. For synthesis of such prepolymers, all OH groups of the polyether polyols were first reacted with hyperstoichiometric amounts of diisocyanates, and the resulting NCO prepolymers were further reacted with a substoichiometric amount of bifunctional compound having a terminal isocyanate-reactive group and another terminal non-isocyanate-reactive group. Such prepolymers may be used, for example, for coating of surfaces.

US 20020042471 A1 and US 20030027921 A1 describe prepolymers having two to six isocyanate groups, which are further modified with a substoichiometric amount of aminosilane. The resulting prepolymers have both NCO groups and silane groups and are used together with a polyol as the coating material.

U.S. Pat. No. 6,423,661 B1 and WO 9955765 A1 describe a polyether-based silyl-terminated prepolymer. For its synthesis, all the OH groups of a polyether polyol are reacted with a hyperstoichiometric amount of isocyanate silane. Such prepolymers are to be used as adhesives.

A similar compound, a six-armed silyl-terminated polyethylene glycol is described in US 2004 0096507 A1.

Hydrogel coatings according to the invention prepared using mixtures of (a) and (b) according to the invention or the mixture of (a) and (b) used in the coatings according to claim 1 effectively prevent adsorption of proteins and cells and may be used for many applications, e.g. in the fields of hygiene and bioanalysis. Therefore, such a use constitutes another subject of the present invention.

A further subject of the present invention is the use of the mixtures of stellate prepolymers according to the invention, their derivatives and/or the mixtures of stellate prepolymers and/or stellate prepolymer-nanoparticle complexes used in the coating agents according to the invention in antisoiling agents for temporary or permanent finishing of surfaces. The main prerequisite for this is hydrophilic surface behavior with a low contact angle hysteresis at the same time. The hydrophilicity of the surface interferes with adsorption and adhesion of soiling that contains protein and fat on the one hand while on the other hand allowing efficient wetting with cleaning agents, so that impurities can be separated from the substrate more easily than is the case with hydrophobic surfaces. The dewetting characterized by the low contact angle hysteresis, i.e. complete runoff of the cleaning solution, also effectively prevents soil redeposition on freshly cleaned surfaces.

Another use of the mixtures of stellate prepolymers according to the invention, their derivatives and/or the mixtures of stellate prepolymers and/or stellate prepolymer-nanoparticle complexes used in the coating agents according to the invention consists of their use as additives in cleaning agents and detergents for hard and soft surfaces such as those used in the sanitation or kitchen areas (machine dishwashing detergent and hand dishwashing agents) to prevent or reduce soiling or soil redeposition, in hair care agents, textile treatment agents, treatment agents for walls, facades and joints, agents for treatment of vehicles such as automobiles, aircraft, ships or boats (antifouling) and in agents for interior and exterior coating of containers to permit, for example, loss-free emptying of containers or in agents for coating bioreactors and heat exchangers, e.g. to prevent adherence of microorganisms.

Another use of the mixtures of stellate prepolymers according to the invention, their derivatives and/or the mixtures of stellate prepolymers used in the coating agents according to the invention and/or stellate prepolymer-nanoparticle complexes is to use them in coatings to prevent the growth and/or crystallization of solids on the surface. In principle, the biological situation in biomineralization processes can be simulated with the hydrogel layers according to the invention due to their dense structure, their hydrophilicity and their easy chemical functionalizability, e.g. by entities. As an example of a typical biomineralization process, the formation of seashells from calcium carbonate can be mentioned; this process is controlled by specifically structured and functionalized hydrophilic polymer layers. Nature teaches that the growth of solids from solution can be promoted or prevented and/or controlled through the details of the chemical structure of such hydrophilic polymers. Crystallization on surfaces may be mentioned here as a growth process that is technologically and economically relevant. The growth of lime can be prevented by the hydrogel layers according to the invention, if necessary by the addition of suitable entities. Beyond the substrate effect described here, lime deposition is also prevented by dewetting of water on the coated surfaces, as mentioned above, which thus prevents crystallization based on this simple physical effect. The hydrogel-based anti-lime coating may be of a permanent or a temporary type.

Through the incorporation of suitable entities, however, it is possible not only to prevent the growth of solids, but on the contrary, it is also possible to induce crystallographically oriented growth of solids on substrates, if necessary, preferably those having functionalities usable in the technology. A general control of the growth of solids is thus possible through the exact details of the chemical composition of the coating, in particular through the entities.

Another use of the mixtures of stellate prepolymers according to the invention, the derivatives thereof and/or the stellate prepolymers and/or stellate prepolymer-nanoparticle complexes used in the mixtures of coating agents according to the invention is in the production of microarrays or sensors for bioanalytical purposes or for coating microfluidic components or for coating microcannulas and capillary systems, e.g. for incorporation of genetic material into cells. The hydrogel coating here allows selective coupling of biomolecules to the coating, on the one hand, if they have receptors bound as an entity, for example, while on the other hand being characterized by a particularly low affinity for nonspecific binding of biomolecules. The hydrogel coatings are therefore particularly suitable as a coating base for substrates for bioanalysis systems.

Subjects of the present invention therefore also include antisoiling agents, cleaning agents and detergents for hard and soft surfaces, hair care agents, textile treatment agents, treatment agents for walls, facades and joints, agents for treatment of vehicles, agents for interior and exterior coating of containers, bioreactors and heat exchangers containing the mixtures of the stellate prepolymers according to the invention and/or the mixtures used in the coatings according to claim 1.

Another use of the mixtures of stellate prepolymers according to the invention, their derivatives and/or the mixtures of stellate prepolymers and/or stellate prepolymer-nanoparticle complexes used in the coating agents according to the invention is for finishing surfaces with modified, in particular reduced, friction properties. For example, if the coatings are applied to textiles, the result is a more pleasant hand, and when used on hair, combability is improved.

The use of these mixtures to prevent static electric charge is the subject of this invention. Stable hydrophilic coatings, e.g. on hair, prevent negative electrostatic effects over long periods of time. The same thing is of course also true of textiles.

Another use of the mixtures of stellate prepolymers according to the invention, their derivatives and/or the mixtures of stellate prepolymers and/or stellate prepolymer-nanoparticle complexes that are used in the coating agents according to the invention consists of fixation and/or retention of dyes on the fibers through the hydrogel coating on textiles either based on the hydrogel structure itself or due to additional functionalities, which are introduced through the aforementioned entities. This yields a color-protective effect which may be utilized, for example, in a no-sort detergent, i.e. a detergent with which both white and colored laundry can be washed.

EXAMPLES

Molecular weights given in the examples are number-average molecular weights of the starting compounds (polyether polyols) that were used to synthesize the prepolymers. The number-average molecular weight of the polyols can be determined computationally by end group determination based on knowledge of the functionality of the compounds or the functionality of the components of the mixture and the OH number of the compound or the mixture (determined according to DIN 53240). For the case when other compounds instead of the polyols are used as the starting compounds, their number-average molecular weight is critical. Thus, for example, the number-average molecular weight of amines can be determined by an end group determination by potentiometric titration according to DIN 16945.

Synthesis of Suitable Stellate Prepolymers

Example 1

Three-armed Triethoxysilyl-terminated Polyether (PP1)

The polyether polyol used here is a three-armed statistical polyethylene oxide-co-propylene oxide having an EO/PO ratio of 75/25 and a number-average molecular of approximately 5000 g/mol, acquired from Dow Chemicals (Voranol® CP 1421). Before the reaction, the polyol was heated to 80° C. in vacuo while stirring for 1 hour.

To the dried polyether polyol (2.04 g, 0.41 mmol) was added slowly (3-isocyanatopropyl)triethoxysilane (317 mg, 1.0 eq.). The reaction mixture was stirred further under a protective gas at 100° C. for two days until the vibrational band of the NCO group had disappeared in an IR measurement. This yields a product in which one triethoxysilyl group is present on each of the free ends of the polymer arms of the stellate prepolymer. The product is a colorless viscous liquid.

Example 2

Six-armed Triethoxysilyl-terminated Polyether (PP2)

The polyether polyol used is a six-armed statistical polyethylene oxide-co-propylene oxide having an EO/PO ratio of 80/20 and a molecular weight of 12,000 g/mol, synthesized by anionic ring-opening polymerization of ethylene oxide and propylene oxide using sorbitol as the initiator. Before the reaction, the polyol was heated to 80° C. in vacuo while stirring for 1 hour.

A solution of polyether polyol (3 g, 0.25 mmol), triethylenediamine (9 mg, 0.081 mmol) and tributyltin dilaurate (9 mg, 0.014 mmol) in 25 mL anhydrous toluene was placed first, then a solution of (3-isocyanato-propyl)triethoxysilane (0.6 mL, 2.30 mmol) in 10 mL anhydrous toluene was added by drops. This solution was stirred further overnight at 50° C. After removing the toluene in vacuo, the crude product was washed repeatedly with anhydrous ether. After vacuum drying, a product having one triethoxysilyl group on each of the free ends of the polymer arms of the stellate prepolymer was obtained as a colorless viscous liquid. IR (film, cm$^{-1}$): 3349 (m, CO—NH), 2868 (s, CH$_2$, CH$_3$), 1719 (s, C=O), 1456 (m, CH$_2$, CH$_3$), 1107 (s, C—O—C), 954 (m, Si—O). $^1$H-NMR (benzene-d$_6$, ppm): 1.13 (d, CH$_3$ of polymer arms), 1.21 (t, CH$_3$ of silane terminal groups), 3.47 (s, CH$_2$ of polymer arms), 3.74 (q, CH$_2$ of silane terminal groups).

Example 3

Six-armed Triethoxysilyl Hydroxy-terminated Polyether (PP3)

As in Example 2, a solution of polyether polyol (10 g, 0.83 mmol) triethylenediamine (30 mg, 0.27 mmol) and dibutyltin dilaurate (30 mg, 0.048 mmol) in 50 mL anhydrous toluene was placed first, then a solution of (3-isocyanatopropyl)triethoxysilane (0.65 mL, 2.49 mmol) in 15 mL anhydrous toluene was added by drops. The solution was stirred further overnight at 50° C. After removing the toluene in vacuo, the crude product was analyzed by IR. The results show that the typical vibrations of the NCO group at approximately 2270 cm$^{-1}$ disappeared completely and, associated with that, reduced OH vibrations could be seen at approximately 3351 cm$^{-1}$, indicating that the isocyanatosilane molecules were successfully linked via a urethane bond at the ends of the polyol. The crude product was then washed repeatedly with anhydrous ether. After vacuum drying, the product was obtained as a colorless viscous liquid, containing triethoxysilyl and hydroxyl groups having a statistical ratio of 3/3 at the free ends of the polymer arms of the stellate prepolymers. IR (film, cm$^{-1}$): 3511 (m, OH), 3351 (m, CO—NH), 2868 (s, CH$_2$, CH$_3$), 1720 (s, C=O), 1456 (m, CH$_2$, CH$_3$) 1112 (s, C—O—C), 953 (m, Si—O). $^1$H-NMR (benzene d$_6$, ppm):

1.08-1.17 (m, CH$_3$ of polymer arms and CH$_3$ of silane end groups), 3.47 (s, CH$_2$ of polymer arms), 3.74 (q, CH$_2$ of silane terminal groups).

Example 4

Six-armed Triethoxysilyl Hydroxy-terminated Polyether (PP4)

As in Example 2, a solution of polyether polyol (10 g, 0.83 mmol) triethylenediamine (30 mg, 0.27 mmol) and dibutyltin dilaurate (30 mg, 0.048 mmol) in 50 mL anhydrous toluene was placed first. Then a solution of (3-isocyanatopropyl) triethoxysilane (0.22 mL, 0.84 mmol) in 15 mL anhydrous toluene was added by drops. The solution was stirred further overnight at 50° C. After removing the toluene in vacuo, the crude product was washed repeatedly with anhydrous ether. After vacuum drying, the product was obtained, having triethoxysilyl groups and hydroxyl groups having a statistical ratio of 1/5 at the free ends of the polymer arms of the stellate prepolymers as a colorless viscous liquid. IR (film, cm$^{-1}$): 3494 (m, OH), 3346 (w, CO—NH), 2868 (s, CH$_2$, CH$_3$), 1722 (m, C=O), 1456 (m, CH$_2$, CH$_3$), 1112 (s, C—O—C), 952 (m, Si—O). $^1$H-NMR (benzene-d$_6$, ppm): 1.08-1.18 (m, CH$_3$ of polymer arms and CH$_3$ of silane end groups), 3.49 (s, CH$_2$ of polymer arms), 3.75 (q, CH$_2$ of silane end groups).

Additional triethoxysilylhydroxy-terminated polyethers were synthesized as done in Examples 3 and 4:

Example 5

Triethoxysilyl Groups and Hydroxyl Groups (Triethoxysilyl/OH Ratio=2/4 PP5)

Colorless viscous liquid. IR (film, cm$^{-1}$): 3496 (m, OH), 3351 (w, CO—NH), 2869 (s, CH$_2$, CH$_3$), 1721 (m, C=O), 1459 (m, CH$_2$, CH$_3$), 1107 (s, C—O—C), 953 (m, Si—O). $^1$H-NMR (benzene-d$_6$, ppm): 1.05-1.16 (m, CH$_3$ of polymer arms and CH$_3$ of silane end groups), 3.47 (s, CH$_2$ of polymer arms), 3.74 (q, CH$_2$ of silane end groups).

Example 6

Triethoxysilyl Groups and Hydroxyl Groups (Triethoxysilyl/OH Ratio=5/1 PP6)

Colorless viscous liquid. IR (film, cm$^{-1}$): 3512 (m, OH), 3351 (w, CO—NH), 2867 (s, CH$_2$, CH$_3$), 1715 (m, C=O), 1457 (m, CH$_2$, CH$_3$), 1116 (s, C—O—C), 952 (m, Si—O). $^1$H-NMR (benzene-d$_6$, ppm): 1.08-1.17 (m, CH$_3$ of polymer arms and CH$_3$ of silane end groups), 3.47 (s, CH$_2$ of polymer arms), 3.74 (q, CH$_2$ of silane end groups).

Example 7

Triethoxysilyl Groups and Hydroxyl Groups (Triethoxysilyl/OH Tatio=4/2 PP7)

Colorless viscous liquid. IR (film, cm$^{-1}$): 3513 (m, OH), 3351 (w, CO—NH), 2867 (s, CH$_2$, CH$_3$), 1721 (m, C=O), 1455 (m, CH$_2$, CH$_3$), 1106 (s, C—O—C), 954 (m, Si—O). $^1$H-NMR (benzene-d$_6$, ppm): 1.05-1.16 (m, CH$_3$ of polymer arms and CH$_3$ of silane end groups), 3.46 (s, CH$_2$ of polymer arms), 3.73 (q, CH$_2$ of silane end groups).

Example 8

Six-armed Triethoxysilyl Isocyanate-terminated Polyether (PP8)

A mixture of the product from Example 2 (4 g, 0.32 mmol), isophorone diisocyanate (IPDI, 3.2 mL, 15.1 mmol) and 7 mL anhydrous toluene was stirred for 48 hours at 50° C. After removing the toluene in vacuo, the crude product was repeatedly washed with anhydrous ether. After vacuum drying, the product, having triethoxylsilyl and isocyanate groups in a statistical ratio of 3/3 on the free ends of the polymer arms of the stellate prepolymers, was obtained as a colorless viscous liquid. IR (film, cm$^{-1}$): 3335 (w, CO—NH), 2869 (s, CH$_2$, CH$_3$), 2266 (s, NCO), 1717 (s, C=O), 1458 (m, CH$_2$, CH$_3$), 1111 (s, C—O—C), 953 (m, Si—O). $^1$H-NMR (benzene-d$_6$, ppm): 1.11-1.18 (m, CH$_3$ of polymer arms and CH$_3$ of silane end groups), 3.49 (s, CH$_2$ of polymer arms), 3.75 (q, CH$_2$ of silane end groups).

Example 9

Six-armed Triethoxysilyl Isocyanate-terminated Polyether (PP9)

A mixture of the product from Example 3 (4.7 g, 0.38 mmol), isophorone diisocyanate (IPDI, 5.65 mL, 26.7 mmol) and 5 mL anhydrous toluene was stirred for 48 hours at 50° C. After removing the toluene in vacuo, the crude product was repeatedly washed with anhydrous ether. After vacuum drying, the product, having triethoxylsilyl and isocyanate groups in a statistical ratio of 1/5 on the free ends of the polymer arms of the stellate prepolymers, was obtained as a colorless viscous liquid. IR (film, cm$^{-1}$): 3335 (w, CO—NH), 2869 (s, CH$_2$, CH$_3$), 2266 (s, NCO), 1717 (s, C=O), 1458 (m, CH$_2$, CH$_3$), 1112 (s, C—O—C), 952 (m, Si—O). $^1$H-NMR (benzene-6, ppm): 1.11-1.18 (m, CH$_3$ of polymer arms and CH$_3$ of silane end groups), 3.48 (s, CH$_2$ of polymer arms), 3.75 (q, CH$_2$ of silane end groups).

According to Examples 8 and 9, the following additional triethoxysilyl-isocyanate-terminated polyethers were synthesized:

Example 10

Triethoxysilyl Groups and Isocyanate Groups (Triethoxysilyl/NCO Ratio=2/4; PP10)

Colorless viscous liquid. IR (film, cm$^{-1}$): 3335 (w, CO—NH), 2869 (s, CH$_2$, CH$_3$), 2265 (s, NCO), 1718 (s, C=O), 1460 (m, CH$_2$, CH$_3$), 1112 (s, C—O—C), 952 (m, Si—O). $^1$H-NMR (benzene-d$_6$, ppm): 1.11-1.17 (m, CH$_3$ of polymer arms and CH$_3$ of silane end groups), 3.48 (s, CH$_2$ of polymer arms), 3.75 (q, CH$_2$ of silane end groups).

Example 11

Triethoxysilyl Groups and Isocyanate Groups (Triethoxysilyl/NCO Ratio=5/1; PP11)

Colorless viscous liquid. IR (film, cm$^{-1}$): 3342 (w, CO—NH), 2869 (s, CH$_2$, CH$_3$), 2265 (s, NCO), 1719 (s, C=O), 1460 (m, CH$_2$, CH$_3$), 1114 (s, C—O—C), 954 (m, Si—O). $^1$H-NMR (benzene-d$_6$, ppm): 1.09-1.17 (m, CH$_3$ of polymer arms and CH$_3$ of silane end groups), 3.48 (s, CH$_2$ of polymer arms), 3.75 (q, CH$_2$ of silane end groups).

Example 12

Triethoxysilyl Groups and Isocyanate Groups (Triethoxysilyl/NCO Ratio=4/2; PP12)

Colorless viscous liquid. IR (film, cm$^{-1}$): 3340 (w, CO—NH), 2869 (s, CH$_2$, CH$_3$), 2265 (s, NCO), 1719 (s, C=O), 1459 (m, CH$_2$, CH$_3$), 1109 (s, C—O—C), 953 (m, Si—O). $^1$H-NMR (benzene-d$_6$, ppm): 1.12-1.17 (m, CH$_3$ of polymer arms and CH$_3$ of silane end groups), 3.49 (s, CH$_2$ of polymer arms), 3.75 (q, CH$_2$ of silane end groups).

Example 13

Six-armed Triethoxysilyl-terminated Polyether (PP13)

The polyether polyol used was a six-armed statistical polyethylene oxide-co-propylene oxide having an EO/PO ratio of approximately 80/20 and a number-average molecular weight of approximately 3000 g/mol, synthesized by anionic ring opening polymerization of ethylene oxide and propylene oxide using sorbitol as the initiator. Before the reaction the polyether polyol was heated to 80° C. in vacuo while stirring for 1 hour.

To the dried polyether polyol (20 g, 6.67 mmol) were added slowly dibutyltin dilaurate (2 mg, 0.01%) and (3-isocyanatopropyl)triethoxysilane (9.5 g, 1.0 eq.). The reaction mixture was stirred further under a protective gas at room temperature for two days until the NCO band disappeared in the IR measurement, yielding a product having one triethoxysilyl group on each of the free ends of the polymer arms of the stellate prepolymers, as a colorless viscous liquid.

Example 14

Mixture of Three-armed Triethoxysilyl-terminated Polyether and Eight-armed Triethoxysilyl-terminated Polyether (PP14)

The polyether polyol mixture used consists of a three-armed statistical polyethylene oxide-co-propylene oxide (glycerol-initiated) and an eight-armed polyether polyol (sucrose-initiated). The polymer arms are each statistical polyethylene oxide-co-propylene oxides with an EO/PO ratio of 75/25. The OH functionality is 6.9 on the average (obtained by end group determination), yielding an average number-average molecular weight of approximately 12,000 g/mol. This yields a ratio of 78 wt % eight-armed polyether polyol to 22 wt % three-armed polyether polyol. The polyether polyol mixture was obtained from the company Dow Chemicals (Voranol® 4053). Before the reaction, the polyether polyol was heated to 80° C. in vacuo while stirring for 1 hour.

Dibutyltin dilaurate (20.9 mg, 0.01%) and (3-isocyanatopropyl)triethoxysilane (30.3 g, 1.0 eq.) were added slowly to dried polyether polyol (209 g, 16.9 mmol). The reaction mixture was additionally stirred for two days at 100° C. under a protective gas until the vibrating band of the NCO group in an IR measurement had disappeared, thus yielding a product in which a triethoxysilyl group is present on each of the free ends of the polymer arms of the two stellate prepolymers. The product is a colorless viscous liquid.

Preparing the hydrogel coatings:

To prepare hydrogel coatings according to the invention and comparative coatings, a portion of the synthesized stellate prepolymers was used individually and/or mixed according to the invention. The prepolymer used and/or the mixture of different prepolymers used (5 wt %) was stirred with water (2.5 wt %) and acetic acid (2.5 wt %) in ethanol at room temperature for 1-2 days. Next, these solutions were diluted with water by a factor of 20 and sprayed onto clean glass surfaces (microscope slides, obtained from Karl Roth GmbH "ready-to-use"). After rinsing with running water, a coating according to the present invention was obtained.

Investigations on hydrogen coatings:

Measurement of the Static Water Contact Angle and the Contact Angle Hysteresis

The measurements were performed using a contact angle measuring device from the company Data Physics GmbH (model OCA20; electronic tilting device TBU90E; electronic spray module ES; software SCA including a software update for SCA module (version 3.11.6 build 155)).

The device is calibrated before measurement by automatic device calibration. With the spray module, one drop of distilled water (15 µL) is applied to the surface of the microscope slide to be measured. The tilt angle is 0° (i.e., the surface to be measured is horizontal). The drop is recorded with a video camera. By means of the software, a tangent to the drop cross section is drawn on the single frame at the point where the drop touches the surface. The resulting angle between the tangent and the surface to be measured is known as the static contact angle (sessile drop method).

The sample together with the sample table and the camera are then tilted up to an angle of 90° at the slowest speed allowed by the device (calculated from the device data: 0.62°/s). During this procedure, a video of the drop is recorded by the camera using the software, so that the tilt angle is also stored at the time of the recording. As soon as the drop begins to run off the surface, the measurement is terminated. Then the advancing angle (angle in the direction of flow of the drop) and the receding angle (on the other side of the drop) can be determined in the video by means of the software using the ellipse method of the measurement software at the time when the drop begins to run off the surface. The difference between the two angles is the contact angle hysteresis (tilting plate method).

Shoe Polish Test

The "shoe polish dirt" was prepared as follows: a mixture of black shoe polish (6.5 wt %), Mazola oil (3.5 wt %), gravy (26 wt %) and tap water (64 wt %) was boiled for two minutes at 100° C. After subsequently stirring for 20 minutes and then cooling to room temperature, shoe polish dirt was obtained. The test surfaces were immersed for two minutes in the shoe polish dirt and then removed and rinsed with running water until the black shoe polish dirt had been completely removed from the surface. The surfaces were then dried at room temperature for one minute. The quantity and distribution of the dirt residue (white fatty layer) remaining on the surface was used as a criterion for the easy-to-clean effect.

IKW Test

The coated glass surface was overlayered with IKW ballast dirt prepared according to the SÖFW Journal 1998, 124, 1029, dried overnight at room temperature, and an untreated glass surface was used as the reference. After drying, the surfaces were washed with running water. The amount and distribution of the dirt residues (white fatty layer) remaining on the surface were used as a criterion for the easy-to-clean effect.

| Coatings | Contact angle $\Theta_{static}$ (degree) | Hysteresis (degree) | Shoe polish test | IKW test |
|---|---|---|---|---|
| PP1 | 44 | 15 | ++ | ++ |
| PP2 | 41 | 9 | ++/+++ | ++/+++ |
| PP1/PP2 (1/4) | 42 | 13 | +++ | +++ |
| PP14 | 45 | 11 | +++ | +++ |

○ = no better than the reference (=uncoated);
+ = moderately better than the reference;
++ = much better than the reference;
+++ = very much better than the reference The pure three-armed stellate prepolymer gave the worst results with respect to contact angle hysteresis, the shoe polish test and the IKW test. Although the pure six-armed stellate prepolymer has good hysteresis, it does not turn out to be optimal with regard to the shoe polish test or the IKW test. Only mixtures of three-armed and six-armed and/or three-armed and eight-armed star polymers yield excellent results with regard to the hysteresis as well as the shoe polish test and the IKW test.

We claim:

1. Coatings having a contact angle hysteresis of water of no more than 20°, measured by the tilting plate method and producible from a mixture comprising at least two different stellate prepolymers and/or stellate prepolymer-nanoparticle complexes, self-crosslinking and crosslinking with the surface of the substrate to be coated,
   wherein the stellate prepolymers and/or stellate prepolymer-nanoparticle complexes have at least three hydrophilic polymer arms prior to crosslinking, wherein each arm is separately water-soluble and has silyl end groups $R^1$ of the following general formula (I) on some or all free ends of the arms:

   $$R^1 \text{ is } -CR^a{}_2-Si(OR^b)_r(R^c)_{3-r} \quad (I)$$

wherein $R^a$ is hydrogen or a linear or branched alkyl group with one to six carbon atoms, $OR^b$ is a hydrolyzable group, $R^c$ is a linear or branched alkyl group with one to six carbon atoms, and r is 1 or 2,
   whereby the silyl end groups $R^1$ are not bound at the end of the polymer arm via a polyisocyanate, and
   wherein polymer arms not having silyl end groups $R^1$ on their free ends optionally have groups on the ends which are reactive with the substrate to be coated, entities optionally introduced into the coating, and/or the silyl end groups,
   with the provision that the mixture contains: (a) at least one stellate prepolymer having three to five hydrophilic polymer arms and (b) at least one stellate prepolymer having at least six hydrophilic polymer arms and/or a stellate prepolymer-nanoparticle complex having at least six hydrophilic polymer arms.

2. Coatings according to claim 1 wherein the stellate prepolymer and/or the stellate prepolymer-nanoparticle complex has a plurality of polymer chains bound to a central unit, the central unit in the case of the stellate prepolymer being a low-molecular organochemical central unit, and in the case of the stellate prepolymer-nanoparticle complex, being an inorganic oxidic nanoparticle,
   wherein the stellate prepolymer and/or stellate prepolymer-nanoparticle complex has the following general formula (II)

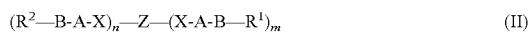
   $$(R^2-B-A-X)_n-Z-(X-A-B-R^1)_m \quad (II)$$

wherein Z is the central unit, which, in the case of stellate prepolymers, determines the number of arms of the stellate prepolymer; A is a hydrophilic, separately water-soluble polymer; B and X are independently a chemical bond or a divalent, low-molecular, organic radical; $R^2$ is not equal to $R^1$ and represents a group that is self-crosslinkable and/or is crosslinkable with $R^1$, and/or is crosslinkable with the substrate, and/or is crosslinkable with the entities optionally introduced into the coating; and m and n are each integers, where m≥1 and n≥0, and m+n have a value from 3 to 100 and corresponds to the number of arms of Z.

3. Coatings according to claim 1, wherein the static water contact angle, determined by the sessile drop method, is no more than 70°.

4. Coatings according to claim 1, wherein the contact angle hysteresis of water, measured by the tilting plate method, is no more than 18°.

5. Coatings according to claim 1, wherein the $OR^b$ radical is an alkoxy radical, and r=1, 2 or 3.

6. Coatings according to claim 2, wherein the $R^2$ radical is chosen from isocyanate radicals, (meth)acrylate radicals, oxirane radicals, alcoholic OH groups, primary and secondary amino groups, thiol groups and silane groups.

7. Coatings according to claim 2, wherein the polymer arms A are chosen from poly-$C_2$-$C_4$-alkylene oxides, polyoxazolidones, polyvinyl alcohols, homopolymers and copolymers containing at least 50 wt % N-vinylpyrrolidone polymerized into them, homopolymers and copolymers containing at least 30 wt % acrylamide and/or methacrylamide polymerized into them, and homopolymers and copolymers containing at least 30 wt % acrylic acid and/or methacrylic acid polymerized into them.

8. Coatings according to claim 2, wherein the stellate prepolymers are obtained by reacting compounds of general formula $Z-(X-A-Y)_{m+n}$, wherein Z, X, A, m and n are as defined in claim 2, and Y is OH or $NH_2$, with silanes that are reactive with the Y group,
   wherein the compounds of general formula $Z-(X-A-Y)_{m+n}$ have a number-average molecular weight in the range of 200 to 50,000 g/mol.

9. Coatings according to claim 1, wherein the entities comprise biologically active substances, pigments, dyes, fillers, silicic acid units, nanoparticles, functional organosilanes, biological cells, receptors, or molecules or cells having receptors, wherein the entities are physically incorporated into the coating or are covalently bonded onto or into them.

10. Method for producing a coating according to claim 1 on a substrate, comprising
    applying a solution of the mixture of (a) and (b) to the substrate to be coated, and
    at least partial crosslinking the silyl end groups and any reactive groups optionally present on the non-silyl-end-group-carrying ends with one another before application to the substrate, during application onto the substrate, or after application onto the substrate.

11. Method according to claim 10, wherein the layer thickness of the coating after the crosslinking reaction is not greater than 1 mm.

12. Coatings according to claim 1, wherein $R^a$ is hydrogen or branched alkyl group with one to six carbon atoms or linear alkyl group with one or three to six carbon atoms.

13. Coatings according to claim 2, wherein n>0.

* * * * *